United States Patent [19]

Aramaki et al.

[11] Patent Number: 5,004,829

[45] Date of Patent: Apr. 2, 1991

[54] METHOD OF PREPARING TRIFLUOROMETHANESULFONIC ACID ANHYDRIDE

[75] Inventors: Minoru Aramaki, Tokyo; Takashi Suenaga; Hiroaki Sakaguchi; Takanori Hamana, both of Ube, all of Japan

[73] Assignee: Central Glass Company, Limited, Ube, Japan

[21] Appl. No.: 506,206

[22] Filed: Apr. 9, 1990

[30] Foreign Application Priority Data

Apr. 10, 1989 [JP] Japan ..................................... 1-90375

[51] Int. Cl.⁵ ..................... B01D 3/34; C07C 303/00; C07C 303/44
[52] U.S. Cl. .................................... 562/113; 562/872; 203/35; 203/38; 203/73; 203/79; 203/80; 203/85; 203/92; 203/DIG. 6; 203/DIG. 25
[58] Field of Search ..................... 203/35, 29, 38, 53, 203/92, 95, 96, 71, 73, 79, 80, 85, DIG. 6, DIG. 25; 562/872, 113

[56] References Cited

U.S. PATENT DOCUMENTS

| | | | |
|---|---|---|---|
| 1,572,766 | 2/1926 | Chevalier et al. | 203/35 |
| 2,489,316 | 11/1949 | Proell | 562/872 |
| 2,732,398 | 1/1956 | Brice et al. | 562/113 |
| 3,829,484 | 8/1974 | Sowerby et al. | 562/872 |
| 3,919,295 | 11/1975 | Wechsberg et al. | 562/113 |
| 4,167,525 | 9/1979 | Kataoka et al. | 203/35 |
| 4,925,975 | 5/1990 | Aramaki et al. | 562/113 |

OTHER PUBLICATIONS

J. Chem. Soc. (1957), by J. Burdon et al., pp. 2574-2578.

*Primary Examiner*—Wilbur Bascomb
*Attorney, Agent, or Firm*—Fleit, Jacobson, Cohn, Price, Holman & Stern

[57] ABSTRACT

$(CF_3SO_2)_2O$ is formed by reaction of $CF_3SO_3H$ with $P_2O_5$ and taken out of the reaction system by distillation, but the residue of the distillation contains a considerable amount of unreacted $CF_3SO_3H$. From the residue unreacted by adding water or a phosphoric acid solution, preferably the latter, to the residue to obtain a fluidic mixture containing an adequate amount of water and subjecting the mixture to distillation, preferably under reduced pressure at temperatures ranging from 180° to 280° C. It is possible to form additional $CF_3SO_3H$ during the recovery process by adding a metal salt of $CF_3SO_3H$ to the aformentioned mixture since the metal salt is decomposed by phosphoric acid contained in the mixture.

17 Claims, No Drawings

METHOD OF PREPARING TRIFLUOROMETHANESULFONIC ACID ANHYDRIDE

BACKGROUND OF THE INVENTION

This invention relates to a method of preparing trifluoromethanesulfonic acid anhydride ($(CF_3SO_2)_2O$) by the dehydrating reaction of trifluoromethanesulfonic acid with phosphorus pentaoxide, and more particularly to a method of industrially preparing the acid anhydride with efficient recovery of unreacted trifluoromethanesulfonic acid.

Trifluoromethanesulfonic acid anhydride is a compound useful as a raw material for the synthesis of medicines, polymerization initiators, etc.

Trifluoromethanesulfonic acid anhydride is prepared usually and almost exclusively by the dehydrating reaction of trifluoromethanesulfonic acid with phosphorus pentaoxide. However, the rate of this reaction becomes extremely low as the conversion of the acid into the acid anhydride reaches about 60%, and hence in industrial practice the dehydrating reaction is terminated at the stage of about 60% conversion. As a natural consequence about 40% of trifluoromethanesulfonic acid subjected reaction remains unreacted in the residue of the reaction system. From an industrial point of view it is necessary to recover and reuse the unreacted acid. Actually, however, the recovery is difficult. First, it is not easy to extract the residue from the reactor since a major portion of the residue is phosphorus pentaoxide in solid form. Further, it is impossible to efficiently recover the acid by subjecting the residue to reduced pressure distillation since the acid in the residue is absorbed in the oxide.

SUMMARY OF THE INVENTION

It is an object of the present invention to provide a method of preparing trifluoromethanesulfonic acid anhydride by the dehydrating reaction of trifluoromethanesulfonic acid with phosphorus pentaoxide and easily and efficiently recovering unreacted trifluoromethanesulfonic acid.

Fundamentally a method according to the invention is reacting trifluoromethanesulfonic acid (abbreviated to TFMSA) with phosphorus pentaoxide, as is usual, and collecting TFMSA anhydride formed by the reaction by distillation. The method further comprises the steps of adding an aqueous solution of phosphoric acid to the residue of the distillation and subjecting a resultant fluidic mixture to distillation to thereby recover unreacted TFMSA.

The addition of a phosphoric acid solution to the residue to the dehydrating reaction renders the residue easy to industrially handle and presumably causes diffusion of unreacted TFMSA impregnated in solid phosphorus pentaoxide into the liquid phase. Then, unreacted TFMSA can be recovered almost entirely by subjecting the mixture of the reaction residue and the phosphoric acid solution to distillation, preferably to reduced pressure distillation at about 180°-280° C.

As a modification, it is possible to use water in place of the aforementioned phosphoric acid solution. However, considering the ease of operations it is preferred to use a phosphoric acid solution.

Optionally and rather preferably, the addition of a phosphoric acid solution or water may be followed by the addition of a metal salt of TFMSA such as potassium or sodium salt. The added salt of TFMSA is decomposed by coexisting phosphoric acid whereby TFMSA is formed. That is, the recovery of unreacted TFMSA is supplemented by the synthesis of TFMSA without significantly modifying the recovering process.

DESCRIPTION OF THE PREFERRED EMBODIMENTS

In reacting TFMSA with phosphorus pentaoxide to form TFMSA anhydride it is suitable to make the molar ratio of the oxide to the acid about 2 to 4 times as high as the stoichiometric ratio. When the proportion of the oxide is smaller the conversion of the acid to its anhydride is too low. When the proportion of the oxide is too large inconvenience is offered to the treatment of the residue of distillation to collect TFMSA anhydride. It is suitable to carry out the reaction between TFMSA and phosphorus pentaoxide at a temperature in the range from room temperature to about 160° C. Usually, in about 3 hr the conversion of TFMSA to its anhydride reaches about 60%, and the rate of the dehydrating reaction becomes too low for further continuing the reaction as a practical operation. Therefore, the reaction is terminated at this stage. TFMSA anhydride formed by the reaction is taken out of the reaction system by distillation.

To recover unreacted TFMSA from the residue of the distillation, the first step is adding an aqueous solution of phosphoric acid or water to the residue. When water is used the addition of water has to be made gradually and very slowly in order to avoid a sharp rise in temperature by the heat of reaction of water with phosphorus pentaoxide. It is preferable to use a phosphoric acid solution, and an optimum concentration of the phosphoric acid solution is about 85 wt% as $P_2O_5$.

The amount of addition of a phosphoric acid solution or water should not be too large. That is, the amount of the phosphoric acid solution or water should be determined such that in the resultant mixture the molar ratio of $H_2O$ to $P_2O_5$ (total of $P_2O_5$ originally contained in the residue of distillation and $P_2O_5$ in the added phosphoric acid solution) is not higher than 2/1 and preferably higher than 1/1. The purpose of so limiting the amount of water is to render the phosphoric acid component of the mixture into pyrophosphoric acid. If the molar ratio of $H_2O$ to $P_2O_5$ in the mixture is increased to about 3/1, orthophosphoric acid exists in the mixture. At temperatures employed in the subsequent distillation of the mixture orthophosphoric acid undergoes dehydrating condensation to liberate water, and the liberated water reacts with TFMSA to form a hydrate higher in boiling point so that the recovery of TFMSA decreases considerably.

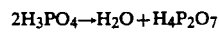

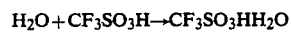

On the other hand, if the amount of water is too small it is difficult to handle the residue of the distillation remaining in the reactor.

In determining the amount of addition of phosphoric acid solution or water it is preferable to take into consideration the quantity of water formed by the dehydrating reaction of TFMSA.

The fluidic mixture prepared by the above treatment is subjected to reduced pressure distillation at temperatures ranging from 180° to 280° C. By this operation unreacted TFMSA in the mixture can easily be recovered to the extent of nearly 100%.

Preferably a metal salt of TFMSA is added to the fluidic mixture in advance of distillation to recover TFMSA. As the metal salt it is suitable to use an alkali metal salt such as potassium salt or sodium salt. The added metal salt of TFMSA is decomposed to TFMSA by phosphoric acid existing in excess. That is, unreacted phosphorus pentaoxide too is effectively utilized. It is suitable to determine the amount of addition of the metal salt of TFMSA such that the molar ratio of the TFMSA salt to $P_2O_5$ in the mixture falls in the range from 0.3:1 to 1:1. Usually TFMSA is prepared by decomposing a metal salt of TFMSA by sulfuric acid. In this invention TFMSA can easily by formed by simply adding a metal salt of TFMSA to the liquid mixture prepared for the recovery of unreacted TFMSA, and TFMSA formed by the decomposition reaction is taken out together with TFMSA recovered by the subsequent distillation operation.

The invention is further illustrated by the following nonlimitative examples.

EXAMPLE 1

The reaction of TFMSA (1597 g) with phosphorus pentaoxide (1007 g) was carried out for 3.5 hr at temperatures ranging from 75° to 90° C. Then, reduced pressure distillation was made at 250–30 mmHg to obtain 920.9 g of TFMSA anhydride. That is, the yield of the anhydride was 61.4%.

To recover unreacted TFMSA from the residue of the distillation, an aqueous phosphoric acid solution containing 85 wt% of $P_2O_5$ was added to the residue so as to obtain a fluidic mixture in which the molar ratio of $H_2O$ to $P_2O_5$ (total of $P_2O_5$ remained unreacted in the residue and $P_2O_5$ in the added phosphoric acid solution) was 2:1. Then the fluidic mixture was subjected to reduced pressure distillation at a pressure of 30 mmHg and at a temperature of 280° C. As the result, the recovery of unreacted TFMSA reached 99.6%. After the recovery of TFMSA the residue of the distillation was still fluidic and easy to handle.

The above process of recovering TFMSA was repeated except that the amount of addition of the phosphoric acid solution was varied so as to vary the molar ratio of $H_2O$ to $P_2O_5$ in the resultant mixture to 1:1, to 3:1 or to 4:1. When the $H_2O/P_2O_5$ molar ratio was 1:1 the recovery of unreacted TFMSA reached 99.8%, but the residue of the distillation was in the form of a dry solid not easy to handle. When the molar ratio was 3:1 the recovery of TFMSA was only 28.0%, and the initial fraction of the distillate was water. When the molar ratio was 4:1 the recovery of TFMSA further decreased to 16.2%, and the initial fraction of the distillate was water.

EXAMPLE 1A

The TFMSA recovery process of Example 1 was modified only in that water was used in place of the phosphoric acid solution. Since water had to be added gradually and very slowly it took a very long time to complete the addition of water. However, there was little difference from Example 1 in the amount of recovery of TFMSA.

EXAMPLE 2

The reaction of TFMSA with $P_2O_5$ was carried out in the same manner as in Example 1. After taking out TFMSA anhydride by distillation, an aqueous phosphoric acid solution containing 85 wt% of $P_2O_5$ was added to the residue such that in the resultant fluidic mixture the molar ratio of $H_2O$ to $P_2O_5$ became 2:1. The mixture was subjected to reduced pressure distillation at a pressure of 30 mmHg by gradually raising temperature. As the distillation temperature was raised the amount of TFMSA recovered as distillate increased in the following manner.

| Temperature (°C.) | Recovery of TFMSA as Distillate (wt %) | Cumulative Recovery of TFMSA (wt %) |
|---|---|---|
| 30–150 | 0 | 0 |
| 150–180 | 0 | 0 |
| 180–200 | 8 | 8 |
| 200–250 | 70 | 78 |
| 250–280 | 21.6 | 99.6 |

EXAMPLE 2

The reaction of TFMSA with $P_2O_5$ was carried out in the same manner as in Example 1. After taking out TFMSA anhydride by distillation, an aqueous phosphoric acid solution containing 85 wt% of $P_2O_5$ was added to the residue such that in the resultant liquid mixture the molar ratio of $H_2O$ to $P_2O_5$ became 2:1. Besides, potassium salt of TFMSA was added to the liquid mixture. The quantity of added $CF_3SO_3K$ was equivalent, by mol, to the quantity of $P_2O_5$ contained in the mixture. The resultant mixture was distilled at a pressure of 30 mmHg and at a temperature of 280° C. As the result, TFMSA obtained as distillate amounted to 97% of the total of unreacted TFMSA and the added potassium salt of TFMSA.

What is claimed is:

1. A method of preparing trifluoromethanesulfonic acid anhydride, comprising the steps of:
   reacting trifluoromethanesulfonic acid with phosphorus pentaoxide and removing trifluoromethanesulfonic acid anhydride formed by the reaction by distillation while leaving a residue of the distillation;
   adding an aqueous solution of phosphoric acid to the residue of said distillation so as to obtain a fluidic mixture; and
   subjecting said fluidic mixture to distillation to thereby recover unreacted trifluoromethanesulfonic acid contained in said residue.

2. A method according to claim 1, wherein the quantity of said aqueous solution of phosphoric acid is such that in said fluidic mixture the molar ratio of $H_2O$ to $P_2O_5$ is not higher than 2/1.

3. A method according to claim 2, wherein said molar ratio is higher than 1/1.

4. A method according to claim 1, wherein the distillation of said mixture is carried out under reduced pressure.

5. A method according to claim 4, wherein the distillation of said mixture is carried out at temperatures ranging from about 180° C. to about 280° C.

6. A method according to claim 1, wherein the concentration of said aqueous solution of phosphoric acid is about 85 wt% as $P_2O_5$.

7. A method according to claim 1, further comprising the step of adding a metal salt of trifluoromethanesulfonic acid to said fluidic mixture for forming trifluoromethanesulfonic acid by the decomposition of said metal salt with phosphoric acid contained in said mixture.

8. A method according to claim 7, wherein said metal salt is an alkali metal salt.

9. A method according to claim 7, wherein the molar ratio of said metal salt to $P_2O_5$ contained in said mixture is in the range from 0.3/1 to 1/1.

10. A method of preparing trifluoromethanesulfonic acid anhydride, comprising the steps of:

reacting trifluoromethanesulfonic acid with phosphorus pentaoxide and removing trifluoromethanesulfonic acid anhydride formed by the reaction by distillation while leaving a residue of the distillation;

adding water to the residue of said distillation so as to obtain a fluidic mixture; and subjecting said fluidic mixture to distillation to thereby recover unreacted trifluoromethanesulfonic acid contained in said residue.

11. A method according to claim 10, wherein the quantity of said water is such that in said fluidic mixture the molar ratio of $H_2O$ to $P_2O_5$ is not higher than 2/1.

12. A method according to claim 11, wherein said molar ratio is higher than 1/1.

13. A method according to claim 10, wherein the distillation of said mixture is carried out under reduced pressure.

14. A method according to claim 13, wherein the distillation of said mixture is carried out at temperatures ranging from about 180° C. to about 280° C.

15. A method according to claim 10, further comprising the step of adding a metal salt of trifluoromethanesulfonic acid to said fluidic mixture for forming trifluoromethanesulfonic acid by the decomposition of said metal salt with phosphoric acid contained in said mixture.

16. A method according to claim 15, wherein said metal salt is an alkali metal salt.

17. A method according to claim 15, wherein the molar ratio of said metal salt to $P_2O_5$ contained in said mixture is in the range from 0.3/1 to 1/1.

* * * * *